US00PP34059P2

(12) United States Plant Patent
Capo

(10) Patent No.: US PP34,059 P2
(45) Date of Patent: Mar. 22, 2022

(54) ***PETUNIA* PLANT NAMED 'KLEPH20491'**

(50) Latin Name: *Petunia hybrida*
Varietal Denomination: KLEPH20491

(71) Applicant: Klemm+Sohn GmbH & Co. KG, Stuttgart (DE)

(72) Inventor: Antonella Capo, Latina (IT)

(73) Assignee: KLEMM+SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 17/376,628

(22) Filed: Jul. 15, 2021

(51) Int. Cl.
*A01H 5/02* (2018.01)
*A01H 6/82* (2018.01)

(52) U.S. Cl.
USPC ..... Plt./356.22
CPC ..... *A01H 6/824* (2018.05)

(58) Field of Classification Search
USPC ..... Plt./356.22
CPC ..... A01H 6/824
See application file for complete search history.

*Primary Examiner* — Anne Marie Grunberg
(74) *Attorney, Agent, or Firm* — Weatherly IP Solutions, LLC; James Weatherly

(57) ABSTRACT

A new *petunia* plant particularly distinguished by smaller flower size with a magenta-purple flower color and a mounding/semi-upright plant habit with a medium vigour, is disclosed.

1 Drawing Sheet

Genus and species: *Petunia hybrida.*
Variety denomination: 'KLEPH20491'.

BACKGROUND OF THE NEW PLANT

The present invention comprises a new and distinct variety of *petunia*, botanically known as *Petunia hybrida* and hereinafter referred to by the variety name 'KLEPH20491'. 'KLEPH20491' is a selection from a cross-pollination of the proprietary female *petunia* line 'PH-2014-0777' (unpatented) and the proprietary male *petunia* line 'PH-2014-0237' (unpatented).

In July of 2016, the proprietary female *petunia* line 'PH-2014-0777' and the male *petunia* line 'PH-2014-0237' were cross pollinated in Latina, Italy and seeds were obtained. The seeds were sown and plants were grown for evaluation. A plant line was selected in April 2017 in Latina, Italy and named 'KLEPH20491'. In May 2017, 'KLEPH20491' was first vegetatively propagated by terminal tip cuttings and tissue culture in Latina, Italy. 'KLEPH20491' was found to reproduce true to type in successive generations of asexual propagation via tissue culture and terminal tip cuttings.

SUMMARY

The following are the most outstanding and distinguishing characteristics of this new variety when grown under normal horticultural practices in Latina, Italy.

1. Magenta-purple flower color;
2. Smaller flower size; and
3. Semi-upright plant habit with a medium vigor.

DESCRIPTION OF THE PHOTOGRAPH

This new *petunia* plant is illustrated by the accompanying photograph, which shows a side view of the flowering plant. The plant is about four months old grown in Stuttgart, Germany in August 2020. The colors shown are as true as can be reasonably obtained by conventional photographic procedures.

DESCRIPTION OF THE NEW VARIETY

The following detailed descriptions set forth the distinctive characteristics of 'KLEPH20491'. The data which define these characteristics were collected from asexual reproductions carried out in Latina, Italy. Data was collected on fourteen-week-old plants grown indoors in Latina, Italy under greenhouse conditions in May 2021. Color references are to The R.H.S. Colour Chart of The Royal Horticultural Society of London (R.H.S.), 5$^{th}$ edition (2007).

Classification:
- *Family.*—Solanaceae.
- *Species.*—*Petunia hybrida.*
- *Common name.*—*Petunia.*
- *Variety.*—'KLEPH20491'.

Parentage:
- *Female.*—Proprietary *petunia* line 'PH-2014-0777'.
- *Male.*—Proprietary *petunia* line 'PH-2014-0237'.

Plant:
- *Form.*—Medium vigor.
- *Habit.*—Semi upright.
- *Height* (*from top of soil*).—23.0 cm.
- *Width* (*horizontal plant diameter*).—55.0 cm.
- *Propagation.*—Vegetative by terminal tip cuttings and tissue culture.
- *Time to produce a finished flowering plant.*—About 13 weeks in winter under short day conditions, about 6 weeks in spring.
- *Time to initiate and develop roots.*—2 to 3 weeks.
- *Root description.*—Moderate density, moderate branching, white roots.

Stems:
- *Average number* (*basal*).—8.
- *Length of basal branches* (*from the base of the stem to the tip*).—30.0 cm.
- *Internode length.*—1.5 cm.

*Diameter of branches* (*from midpoint*).—0.2 cm.
*Stem color.*—RHS 144A.
*Anthocyanin.*—Absent.
*Texture.*—Pubescent.

Leaves:
*Arrangement.*—Alternate along the stem and opposite under the inflorescence.
*Length.*—3.5 cm.
*Width.*—2.0 cm.
*Shape.*—Elliptic.
*Apex.*—Acute.
*Base.*—Attenuate.
*Margin.*—Entire.
*Immature leaf color.*—Upper surface: RHS 137C. Lower surface: RHS 138B.
*Mature leaf color.*—Upper surface: RHS 137A. Lower surface: RHS 146B.
*Texture.*—Upper surface: Pubescent. Lower surface: Pubescent.
*Venation pattern.*—Arcuate.
*Venation color.*—Upper surface: RHS 137A. Lower surface: RHS 146B.
*Petioles.*—Length: 0.4 cm. Diameter: 0.35 cm. Color: RHS 144B. Texture: Pubescent.

Flower bud:
*Shape.*—Irregularly oblong.
*Length.*—4.0 cm.
*Diameter.*—0.7 cm.
*Color at tight bud.*—RHS N79A.
*Texture.*—Pubescent.

Inflorescence:
*Blooming habit* (*flowering season*).—Continuously flowering during spring and summertime.
*Inflorescence type.*—Sympodial, with monochasial growth.
*Number of flowers per node.*—1.
*Lastingness of individual blooms on the plant.*—About 10 days.
*Fragrance.*—Absent.
*Flowers.*—Arrangement: Composed of 5 fused petals. Diameter (flower face): 6.0 cm. Depth (total length of flower): 5.5 cm. Throat/Funnel: Length: 2.7 cm. Diameter (at opening): 1.0 cm. Texture: Inner surface: Smooth. Outer surface: Pubescent. Color: Inner surface: RHS N187A. Outer surface: RHS N77A. Petals: Color, mature flower (fully opened): Upper surface: RHS a bit darker than N74A. Lower surface: RHS N78B. Apex: Cuspidate. Base: Fused. Shape: Salverform. Margin: Entire. Strength of waviness: Weak. Degree of lobation: Medium.
*Calyx arrangement.*—Whorl of 5 sepals, fused at the base. Sepals: Color: Upper surface: RHS N137B. Lower surface: RHS 137C. Length: 1.4 cm. Width: 0.25 cm. Shape: Linear. Apex: Rounded. Base: Attenuate. Margin: Entire. Texture: Upper surface: Pubescent. Lower surface: Pubescent.
*Pedicels.*—Color: RHS 144B. Length: 2.2 cm. Diameter: 0.15 cm. Texture: Pubescent.

Reproductive organs:
*Stamens.*—Quantity: 5. Shape: Needle with oblong head. Filament: Length: 1.4 cm. Diameter: 0.15 cm. Color: RHS 85B. Anther: Shape: Oblong. Color: RHS 85A. Length: 0.2 cm. Diameter: 0.15 cm. Pollen: Color: RHS 92A. Amount: Moderate.
*Pistils.*—Quantity per flower: 1. Length: 2.2 cm. Stigma color: RHS N189A. Style color: RHS 79B.

Fruit and seed set: None observed.
Disease and pest/insect resistance: None observed.

COMPARISON WITH PARENTAL LINES AND KNOWN VARIETY

'KLEPH20491' is a distinct variety of *petunia*. 'KLEPH20491' is distinguished from its parents as described in Table 1 and Table 2:

TABLE 1

Comparison with Female Parental Line

| Characteristic | Variety 'KLEPH20491' | Female parent 'PH-2014-0777' |
|---|---|---|
| Flower color | Magenta purple | Light pink |

TABLE 2

Comparison with Male Parental Line

| Characteristic | Variety 'KLEPH20491' | Male Parent 'PH-2014-0237' |
|---|---|---|
| Flower size | Smaller than the male parent | Bigger than KLEPH20491 |

'KLEPH20491' is most similar to the commercial *petunia* plant named 'AlpeTunia Dark Purple' (not patented). Differences between the two varieties are described in Table 3:

TABLE 3

Comparison with Similar Variety

| Characteristic | Variety 'KLEPH20491' | Commercial line 'AlpeTunia Dark Purple' |
|---|---|---|
| Plant habit and vigour | Semi-upright, medium vigour | Trailing and vigorous |

I claim:

1. A new and distinct variety of *petunia* plant named 'KLEPH20491' as illustrated and described herein.

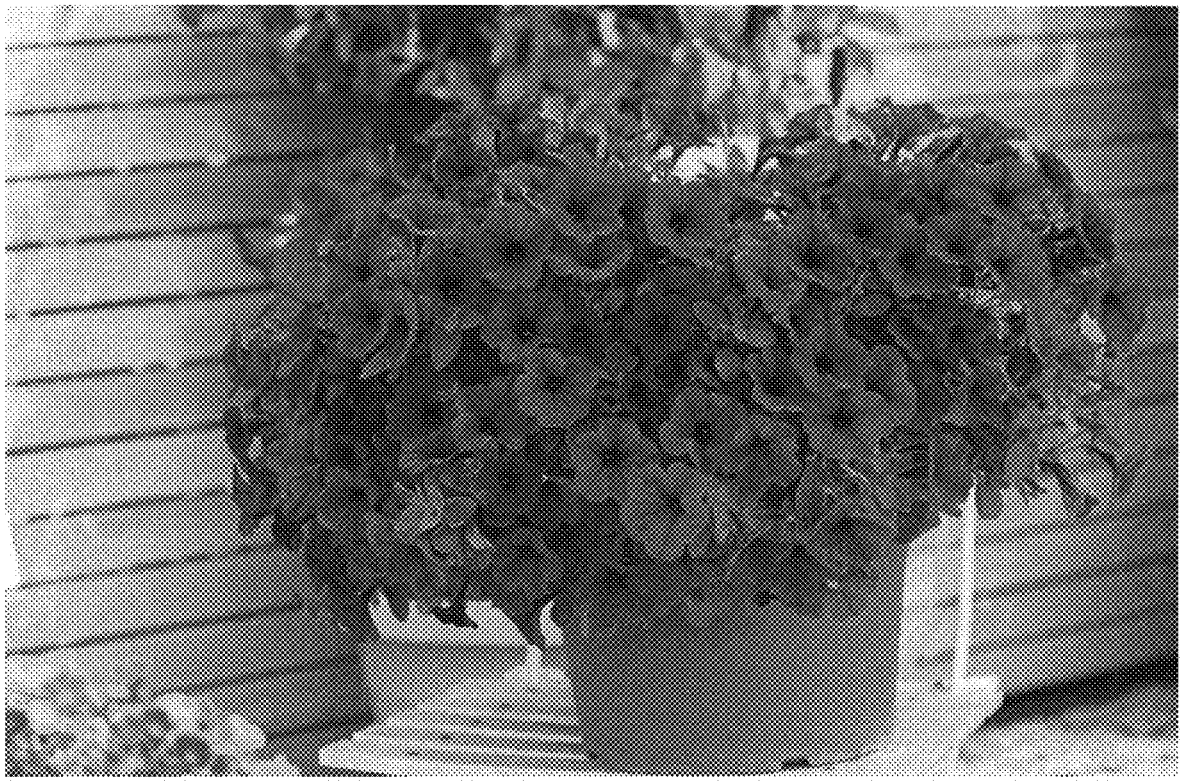

* * * * *